United States Patent [19]

Gray et al.

[11] Patent Number: 5,792,189
[45] Date of Patent: Aug. 11, 1998

[54] DEFIBRILLATION UTILIZING THE DOMINANT FREQUENCY OF FIBRILLATION

[75] Inventors: Richard A. Gray, Vestavia Hills, Ala.; Jose Jalife, Manlius, N.Y.

[73] Assignee: The Research Foundation of State University of New York, Albany, N.Y.

[21] Appl. No.: 835,118

[22] Filed: Apr. 4, 1997

[51] Int. Cl.$^6$ ...................................... A61N 1/39
[52] U.S. Cl. ...................................... 607/5; 607/73
[58] Field of Search ...................................... 607/5, 68, 69, 607/73, 76, 4

[56] References Cited

U.S. PATENT DOCUMENTS

| | | |
|---|---|---|
| 4,637,397 | 1/1987 | Jones et al. . |
| 4,800,883 | 1/1989 | Winstrom . |
| 4,821,723 | 4/1989 | Baker, Jr. et al. . |
| 4,974,600 | 12/1990 | Reyes . |
| 5,161,528 | 11/1992 | Sweeney ...................... 607/5 |
| 5,199,429 | 4/1993 | Kroll et al. . |
| 5,245,660 | 9/1993 | Pecora et al. ................ 380/48 |
| 5,324,309 | 6/1994 | Kallok ........................... 607/5 |
| 5,352,239 | 10/1994 | Pless ............................. 607/5 |
| 5,379,346 | 1/1995 | Pecora et al. ................ 380/48 |
| 5,395,393 | 3/1995 | Wickham ..................... 607/5 |
| 5,402,334 | 3/1995 | Pecora et al. ............... 364/158 |
| 5,411,525 | 5/1995 | Swanson et al. ............. 607/5 |
| 5,413,591 | 5/1995 | Knoll ............................ 607/6 |
| 5,522,853 | 6/1996 | Kroll ............................. 607/5 |
| 5,620,468 | 4/1997 | Mongeon et al. ............ 607/5 |
| 5,632,267 | 5/1997 | Hognelid et al. ............. 607/5 |
| 5,662,687 | 9/1997 | Hedberg et al. ............. 607/5 |

FOREIGN PATENT DOCUMENTS 0 588 127 A1  3/1994  European Pat. Off. ......... A61N 1/39

OTHER PUBLICATIONS

Carroll, T.L. and Pecora, L.M., "Using chaos to keep period-multiplied systems in phase", Physical Review E, vol. 48, No. 4, Oct. 1993, pp. 2426–2436.

Garfinkel, A., Spano, M.L., Ditto, W.L., and Weiss, J.N., "Controlling Cardiac Chaos", Science, vol. 257, 28 Aug. 1992, pp. 1230–1235.

Heagy, J.F., Carroll, T.L. and Pecora, L.M., "Synchronous chaos in coupled oscillator systems", Physical Review E, vol. 50, No. 3, Sep. 1994, pp. 1874–1884.

Kapitaniak, T., Chua, L.O. and Zhong, G-Q., "Experimental Synchronization of Chaos Using Continuous Control", International Journal of Bifurcation and Chaos, vol. 4, No. 2, 1994, pp. 483–488.

Gray, Ph.D., R.A., Foster, E., Jalife MD, J., "Entrainment of the Intact Ventricles Using Field Stimulation", PACE, vol. 19, No. 4, Part II, Apr. 1996, p. 66.

Primary Examiner—William E. Kamm
Assistant Examiner—George R. Evanisko
Attorney, Agent, or Firm—Heslin & Rothenberg, P.C.

[57] ABSTRACT

Method and apparatus are provided for cardiac defibrillation using a waveform with a dominant frequency near that of a fibrillating heart. The defibrillator includes electrical generating means for producing a waveform having a dominant frequency within a range of 2 Hz–20 Hz. The waveform provides low level electrical shock to a fibrillating heart, thereby causing defibrillation. The waveform, which can comprise a Rossler-type chaotic waveform or a sinusoidal waveform, preferably has a dominant frequency near the frequency of fibrillation of the fibrillating heart.

17 Claims, 9 Drawing Sheets

DEFIBRILLATION UTILIZING THE DOMINANT FREQUENCY OF FIBRILLATION

STATEMENT AS TO RIGHTS UNDER FEDERALLY SPONSORED RESEARCH

This invention was made with government support under contract number 5PO1 HL3970705 awarded by the National Institute of Health. Accordingly, the U.S. Government has certain rights in the invention.

TECHNICAL FIELD

The present invention relates generally to methods and apparatus for cardiac defibrillation, and more particularly, to methods and apparatus which use waveforms with a dominant frequency near that of a fibrillating heart to effectuate defibrillation.

BACKGROUND OF THE INVENTION

During fibrillation, sections of conductive cardiac tissue of the affected chamber undergo completely uncoordinated random contractions, quickly resulting in a loss of synchronous contraction of the overall mass of tissue and a consequent loss of the blood-pumping capability of that chamber. Because of a lack of contribution of the atrial chambers to cardiac output, atrial fibrillation is hemodynamically tolerated and not generally regarded as life-threatening. However, in the case of ventricular fibrillation, cardiac output ceases instantaneously as a result of the rapid, turbulent electrical and mechanical activity of the excitable myocardial tissue and the consequent ineffectual quivering of the ventricles. Unless cardiac output is restored almost immediately after the onset of ventricular fibrillation, tissue begins to die for lack of oxygenated blood, and death will occur within minutes.

Since ventricular fibrillation is frequently triggered by acceleration of ventricular tachycardia, various methods and devices have been developed or proposed to treat and arrest the tachycardia before the onset of fibrillation. Conventional techniques for terminating tachycardia include pacing therapy and cardioversion. In the later technique, the heart is shocked with one or more current or voltage pulses of generally considerably higher energy content than is delivered in pacing pulses. Unfortunately, the therapy itself presents a considerable risk of precipitating fibrillation.

Defibrillation—that is, the method employed to terminate fibrillation—generally involves applying one or more high energy "countershocks" to the heart in an effort to overwhelm the turbulent contractions of individual tissue sections and to re-establish an organized spreading of action potential from cell to cell of the myocardium, thereby restoring the synchronized contraction of the mass of tissue. If these turbulent contractions continue in any tissue section, the defibrillation may be short-lived with a region of tissue being a source for re-fibrillation. Successful defibrillation clearly requires the delivery of a shocking pulse containing a substantial amount of electrical energy to the heart of the affected person, at least adequate to terminate the fibrillation and to preclude an immediate re-emergence. Although high intensity defibrillation shocks are often successful in arresting fibrillation, they tend to precipitate cardiac arrhythmias, which themselves may accelerate into fibrillation. Moreover, the high intensity shocks can cause permanent myocardial injury.

In the conventional approach of transthrracic external defibrillation, paddles are positioned on a patient's thorax and approximately 100–400 joules of electrical energy is delivered to the chest area in the region of the heart. It is apparent that, from the manner in which the shock is applied, only a portion of this energy is actually delivered to the heart and, thus, is available to arrest fibrillation. Where fibrillation occurs during open heart surgery, internal paddles may be applied to opposite surfaces of the ventricular myocardium and, in these instances, the energy required to be delivered is considerably less, on the order of 20–40 joules.

Recently, implantable automatic defibrillators have been developed for use in detecting and treating ventricular fibrillation. See, for example, U.S. Pat. No. 4,254,775 to Langer and U.S. Pat. No. 4,384,585 to Zipes. As of today, a vast number of improvements in implantable defibrillators, including fibrillation detectors and high energy pulse generators with related electrode configurations, have been reported in the scientific literature and the patent publications.

The pulse energy required for internal ventricular defibrillation with known implanted defibrillators and electrode systems ranges from about 25 joules to 40 joules. Of course, the actual energy level required may differ from patient to patient, and further depends on such factors as the type of pulse waveform and the electrode configuration employed. Currently, implantable defibrillators are being tested to also treat atrial fibrillation. The energy required to defibrillate the atrium is 0.6 to 2 joules, however, during atrial fibrillation patients are conscious and even these low energy shocks can be intolerably painful for some people.

While advances and improvements in electrical energy sources in general and pacemaker batteries in particular have been made over the past few years, it is clear nonetheless, that repeated delivery of such amounts of energy from an implanted system will deplete conventional batteries in relatively short order. Accordingly, for this and other reasons mentioned above, reduction of energy levels required for internal defibrillation remains a significant area of inquiry and investigation.

Prior defibrillators have commonly employed systems to produce unidirectional (monophasic) shock impulses. However, the use of unipolar pulses has been known to produce certain undesirable side effects including damage to the heart tissue near the electrode sites, induction of certain post shock arrhythmias, and changes in the S-T segment. Moreover, under certain circumstances, some pulses are not effective to arrest ventricular fibrillation.

Recent medical research has shown that many of the problems associated with unipolar cardioverting pulses are alleviated when multiphasic cardioverting pulse trains are employed. For example, bidirectional (or biphasic) waveforms decrease required defibrillation shock strengths and reduce post shock cardiac arrhythmias over monophasic pulses. Triphasic wave defibrillation has also been proposed in the art, for example, reference U.S. Pat. No. 4,637,397.

While methods and apparatus incorporating various defibrillation concepts and associated pulses have been used with success, it is considered desirable to further improve upon the known defibrillation waveforms. The subject invention is directed to meeting this need.

DISCLOSURE OF THE INVENTION

The invention comprises in one aspect a method for defibrillating a heart in fibrillation which includes the steps of: detecting fibrillation of the heart; and responsive to the detecting, applying to the fibrillating heart a repeating waveform having a dominant frequency within the range of 2

Hz–20 Hz. Preferably, the dominant frequency is near the frequency of fibrillation of the fibrillating heart, i.e., approximately 10 Hz. In one embodiment, the waveform can comprise a Rossler-type chaotic waveform, while in an alternate embodiment, the waveform could be sinusoidal shaped.

In another aspect, the invention comprises a defibrillator for defibrillating a fibrillating heart. The defibrillator includes electrical generating means for producing a repeating waveform having a dominant frequency within a range of 2 Hz–20 Hz. The defibrillator further includes means for delivering the waveform to provide electrical shock to the fibrillating heart, thereby causing defibrillation of the heart.

Applicants have experimentally and theoretically shown that a low frequency sinusoidal or chaotic Rossler-type waveform can be used to defibrillate cardiac tissue. The precise shape and duration of the waveform do not appear to be critical for lowering the defibrillation threshold. The significant aspect to lowering the threshold is that the waveform has a dominant frequency near the dominant frequency of the fibrillation episode. The most effective waveforms exhibit a dominant frequency near 10 Hz, but within a range of 2 Hz–20 Hz is believed practical. By decreasing the fibrillation threshold, smaller battery packs can be used in internal cardiac defibrillators. In addition, by lowering the threshold, a patient is subjected to less pain, and there is less damage to heart tissue.

BRIEF DESCRIPTION OF THE DRAWINGS

The above-described objects, advantages and features of the present invention, as well as others, will be more readily understood from the following detailed description of certain preferred embodiments of the invention, when considered in conjunction with the accompanying drawings in which:

FIG. 1b is the frequency spectrum of the ECG of FIG. 1a;

FIG. 7b is the frequency spectrum of the waveform of FIG. 7a;

FIG. 8b is the frequency spectrum of the waveform of FIG. 8a; and

FIG. 9 is a diagram of a circuit for generating the Rossler-type chaotic waveform of FIGS. 3b and 8a;

BEST MODE FOR CARRYING OUT THE INVENTION

Presented herein are certain novel waveforms for stimulating cells in arrhythmic myocardial tissues in accordance with the present invention. As noted initially, during tissue arrhythmia, various cells or groupings of cells are depolarized at various times. This results in uncoordinated twitching of individual muscular fibers with little or no movement of the muscle as a whole. The condition is commonly referred to as fibrillation. It is well known that an appropriate electric shock, such as a monophasic, biphasic or triphasic signal, applied to the cells of fibrillating myocardial tissues will often realign the cells.

A novel waveshape in accordance with the present invention comprises a waveform having a dominant frequency in the range of 2 Hz–20 Hz. The waveform may comprise a sinusoidal waveform, or more preferably, a Rossler-type chaotic waveform. Rossler-type chaotic waveforms are described in the art, for example, reference an article by Carroll and Pecora entitled "Using Chaos to Keep Period-multiplied Systems in Phase", Physical Review E, Vol. 48, No. 4, pp. 2426–2436 (1993), which is hereby incorporated herein in its entirety.

Figure 1A:
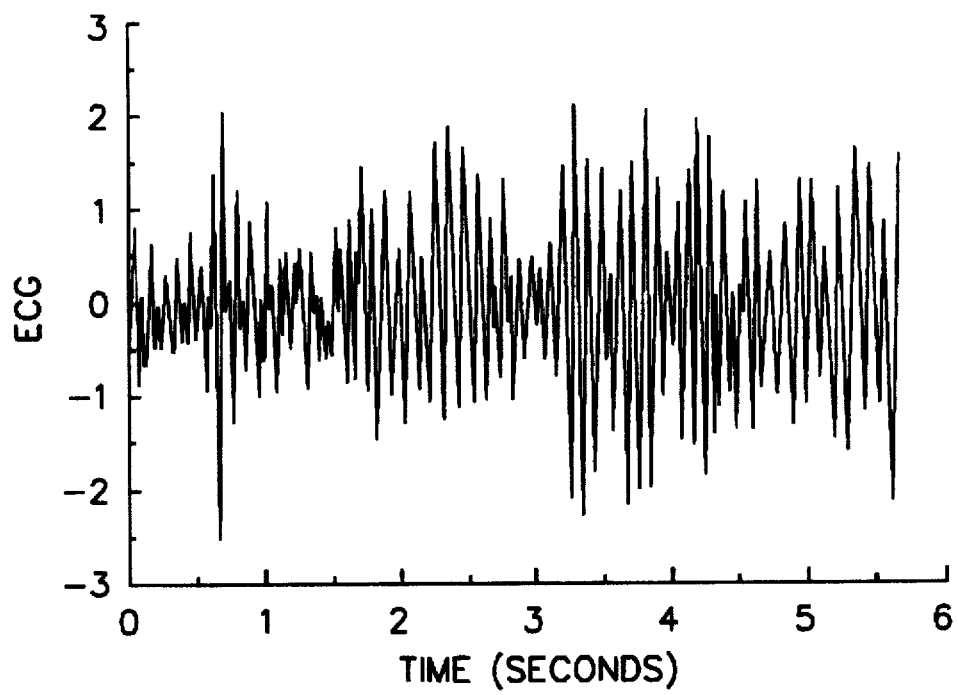
FIG. 1a is a graph of an electrocardiogram (ECG) of a fibrillating heart.
Figure 1B:
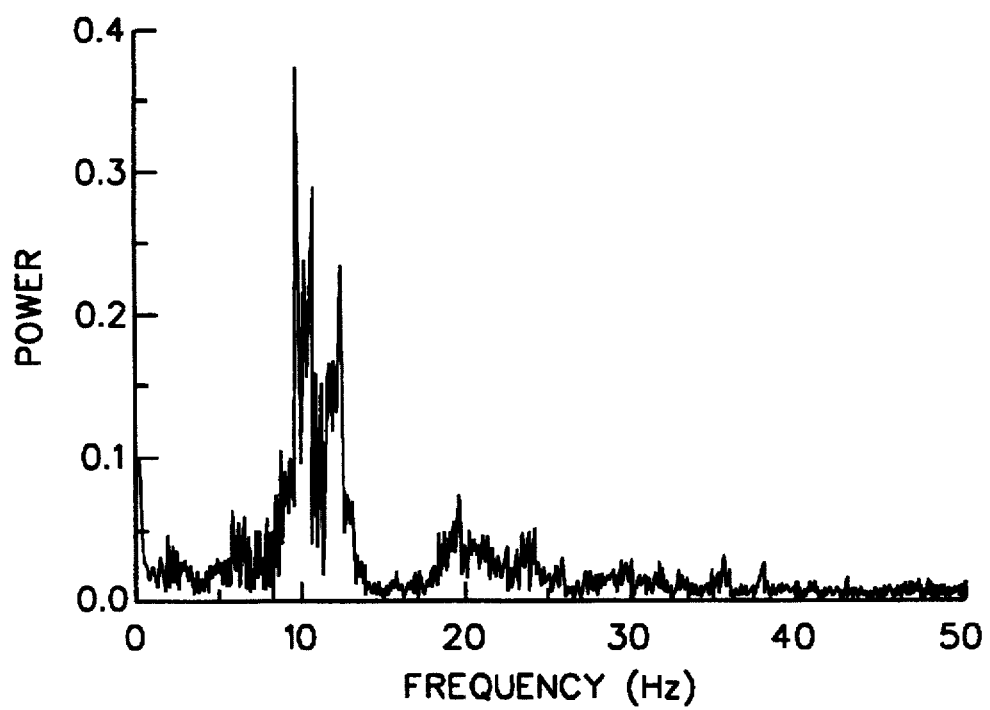

FIG. 1a is a sample electrocardiogram (ECG) recorded from a heart during fibrillation. The ECG exhibits irregular morphology and period. FIG. 1b comprises the frequency spectrum of the ECG demonstrating that the dominant frequency components during fibrillation are centered near 10 Hz. Thus, although irregular, there is a dominant frequency component. A defibrillation waveform in accordance with this invention employs this recognition by requiring that the drive signal itself have a dominant frequency near 10 Hz, although a dominant frequency anywhere in the range 2–20 Hz is believed workable. The use of a repeating defibrillation waveform having a dominant frequency near the dominant frequency of the fibrillation episode results in a decrease in the average power needed to defibrillate the heart. As noted above, this can allow smaller battery packs to be used in an implantable cardioverter-defibrillator, can cause less pain to the patient (which can be significant for atrial defibrillation), and results in less damage to heart tissue.

Figure 2A:
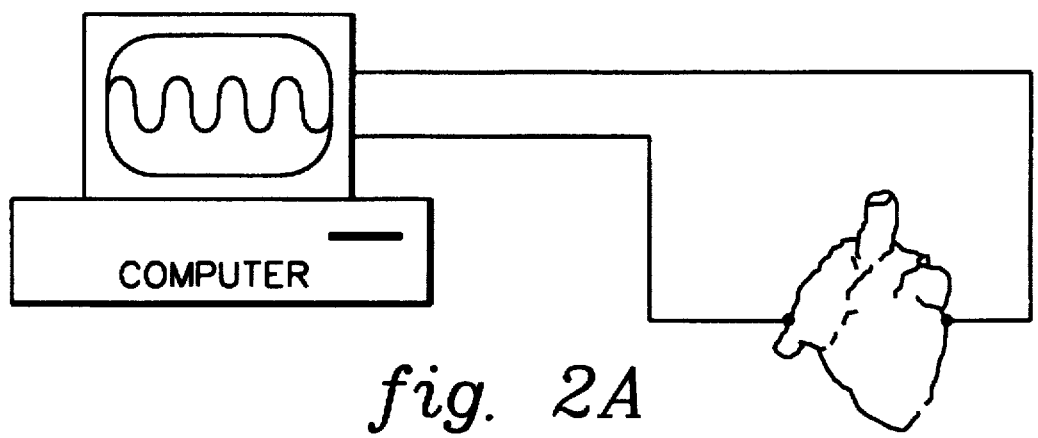
FIG. 2a is a diagram of a sinusoidal waveform being applied to a heart for defibrillation in accordance with the present invention.
Figure 2B:
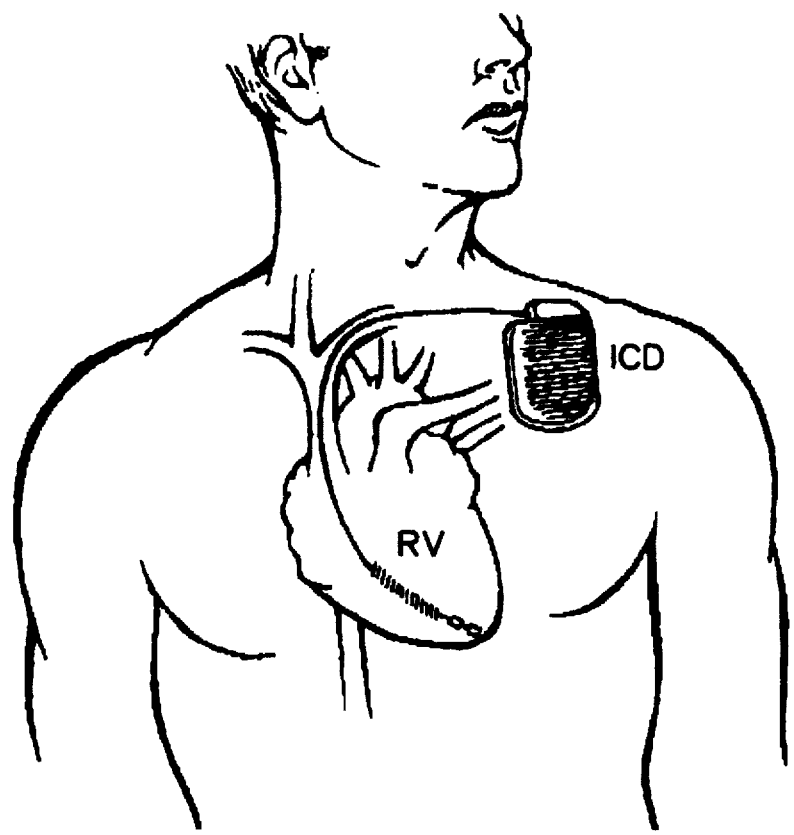
FIG. 2b is a diagram of an internal automatic defibrillator to use the dominant frequency of fibrillation in accordance with the present invention.

FIG. 2a depicts the application to a heart, via electrodes, of a periodic waveform in accordance with this invention. In this depiction, the periodic waveform comprises a sinusoidal waveform which would have a frequency in the range of 2–20 Hz, and preferably at or near 10 Hz. FIG. 2a is generic in that it is intended to represent the application of a waveform in accordance with this invention either by externally applied electrodes or an implantable automatic defibrillator, both of which can be constructed by those skilled in the art so as to employ a defibrillation waveform pursuant to this invention based upon the information presented herein. One embodiment of an internal automatic defibrillator is depicted in FIG. 2b for completeness.

Figure 3A:
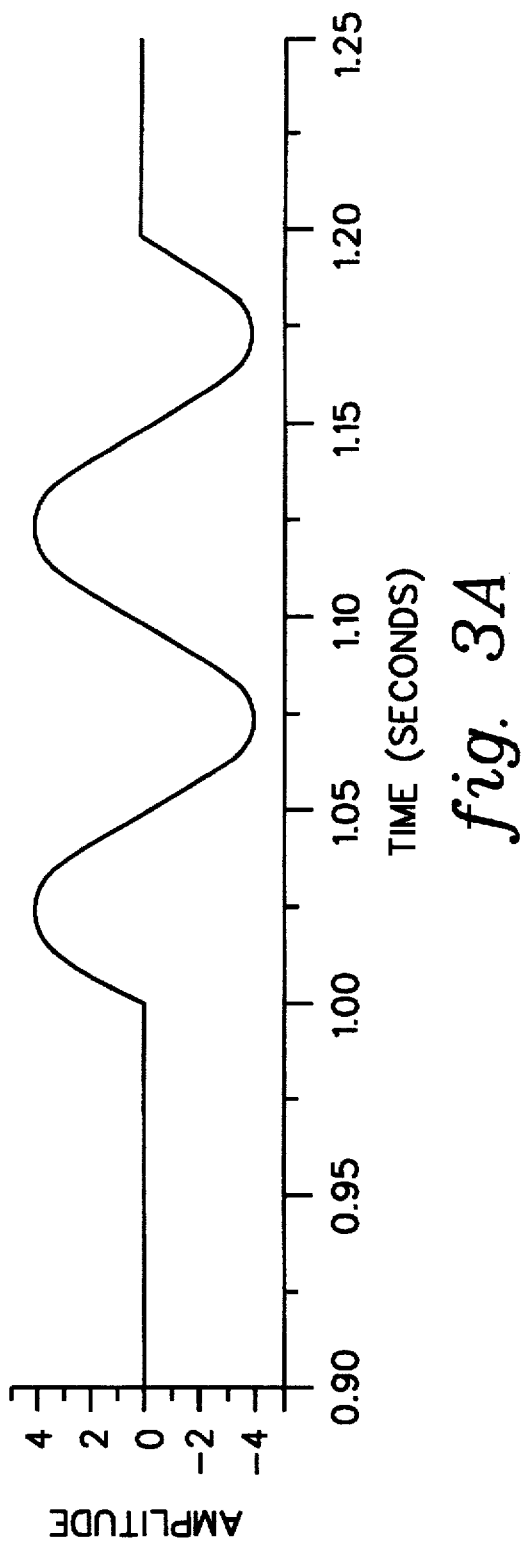
FIG. 3a is a graph of a sinusoidal waveform at 10 Hz with a duration of 0.2 seconds for defibrillation in accordance with the present invention.
Figure 3B:
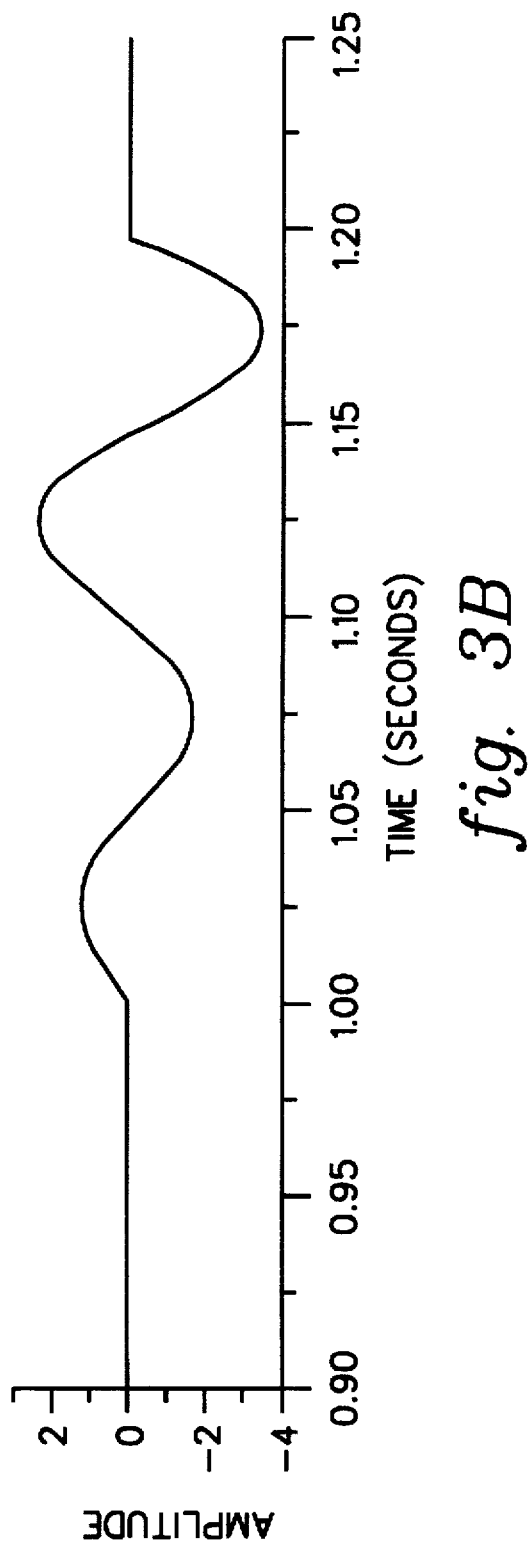
FIG. 3b is a graph of a chaotic waveform employed in a defibrillator in accordance with the present invention, the chaotic waveform having a dominant frequency near 10 Hz and a duration of 0.2 seconds.

FIGS. 3a & 3b depict two waveshapes useful as defibrillation signals in accordance with the present invention. Both waveshapes are shown to be approximately 0.2 seconds in length, which is significantly longer duration than conventional monophasic or biphasic pulses (which are approximately 0.01 seconds). Applicants have discovered that low frequency waveforms with a dominant frequency between 2–20 Hz and in particular near 10 Hz, act on the heart by a different mechanism than the conventional short duration (DC) waveforms of a monophasic, biphasic or triphasic signal.

Applicants conducted experiments on the efficacy of chaotic and sinusoidal waveforms with a dominant frequency of 10 Hz. These experiments were carried out employing hearts isolated from New Zealand rabbits (≈3.0 kg) anesthetized with sodium pentobarbital (35 mg/kg). After excision, the hearts were connected to a Langendorff apparatus for perfusion of warm (36°–38° C.) Tyrode's solution buffered to a pH of 7.4, under a pressure head of 50–60 mm Hg at a rate of 50–60 ml/min. The solution consisted of the following (mM): NaCl, 148; KCl, 5.4; $CaCl_2$, 1.8; $MgCl_2$, 1.0; $NaHCO_3$, 5.8; $NaH_2PO_4$, 0.4; and glucose, 5.5. An ECG was recorded from two leads on the heart surface, and was passed through an isolated preamplifier and bandpass filter (0.05–300 Hz). The ECG recordings were displayed on an oscilloscope, digitized at 2 kHz and transferred to a computer via an A/D board. Induction of fibrillation was achieved using a bipolar electrode located on the heart surface to apply high frequency or programmed stimulation with a strength of 1–2 volts. Defibrillation shocks were applied by passing current through titanium mesh band electrodes based on the design by Dillon described in an article entitled "Synchronized Repolarization After Defibrillation Shocks: A Possible Component of the Defibrillation Process Demonstrated by Optical Recordings in Rabbit Hearts," Circulation 85:1865–1878 (1992). The voltage across the heart and the heart resistance were measured during the shock.

Figure 4:
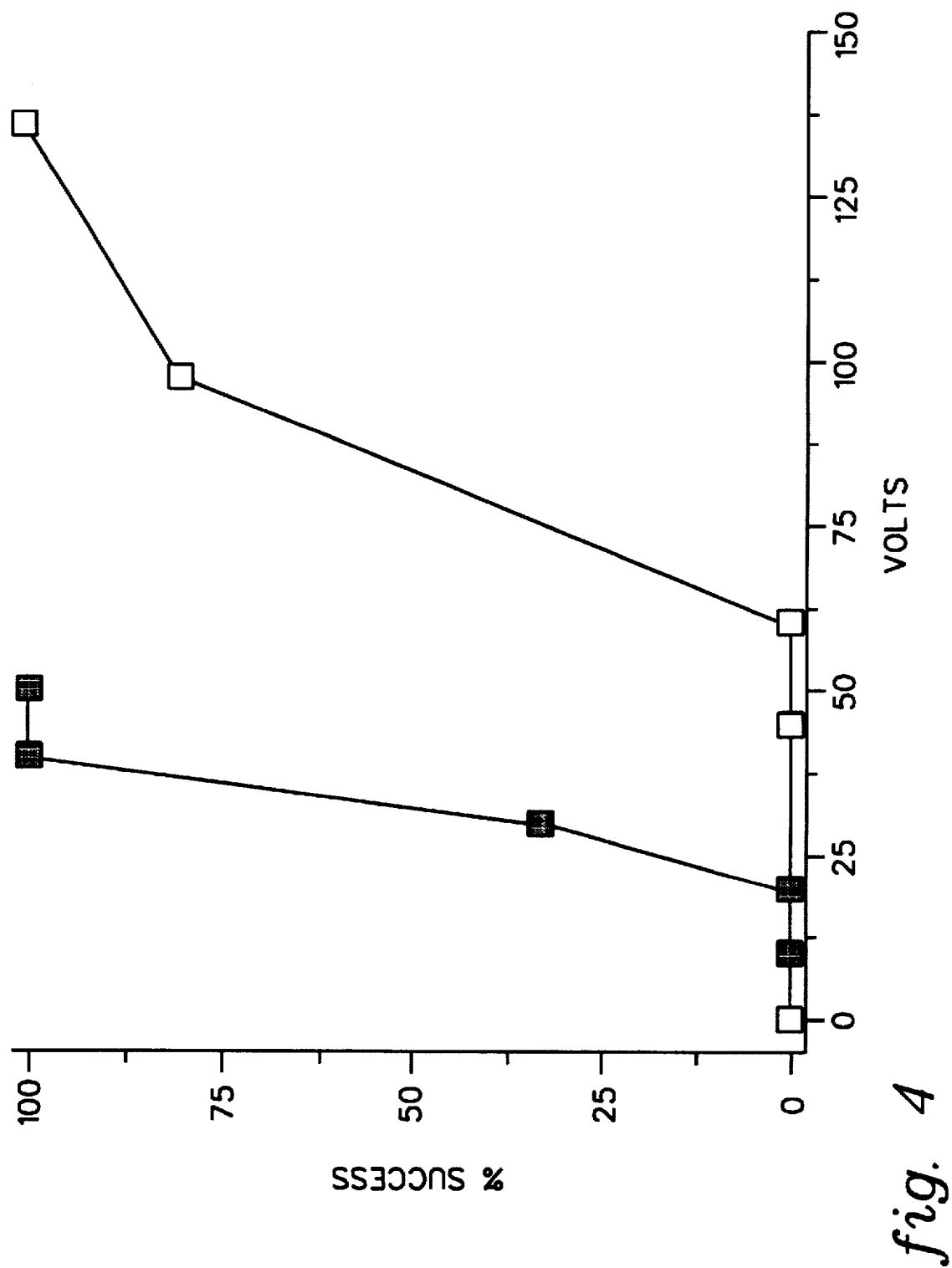
FIG. 4 is a graph of the probability of successful defibrillation of a rabbit heart using the chaotic waveform of FIG. 3b (filled symbols) compared with a convention monophasic waveform (open symbols)

A stimulator, made up of a computer with a D/A board along with a high voltage amplifier capable of generating arbitrary waveforms at high energies, was used to deliver the shocks. Defibrillation thresholds were determined by giving shocks at five strengths ranging from 10–60 volts in 10 volt increments. Five shocks at each voltage were given in a down-up-down-up-down protocol and randomizing the sequence of waveforms for each strength. Percent success versus voltage curves were constructed for each waveform for each animal. These curves were fit to a sigmoid curve to determine the peak voltage calculated as the voltage corresponding to 50% success. Results from these experiments suggest that our chaotic and sinusoidal waveforms with a dominant frequency of 10 Hz lower the voltage required to terminate fibrillation. Percent success versus voltage relationships were well fit by sigmoid curves. Overall, in the rabbit heart, the peak voltage was 33.1±5.5 volts for the chaotic waveform and 33.8±8.3 volts for the sinusoidal waveform compared with 66.5 volts for a monophasic waveform. Other laboratories report peak voltage from monophasic shocks ranging from 63–79 volts. Thus, the peak voltage for the chaotic and sinusoidal waveforms with a dominant frequency of 10 Hz is approximately 50% of that required for monophasic waveforms. Because defibrillation is probablistic, defibrillation thresholds are determined by calculating the efficacy (% success) versus voltage. This relationship is shown in FIG. 4 for the chaotic waveform (filled symbols) depicted in FIG. 3b and a conventional monophasic waveform (open symbols). These results confirm that a chaotic waveform having a dominant frequency near 10 Hz lowers the voltage required to terminate fibrillation.

Figure 5:
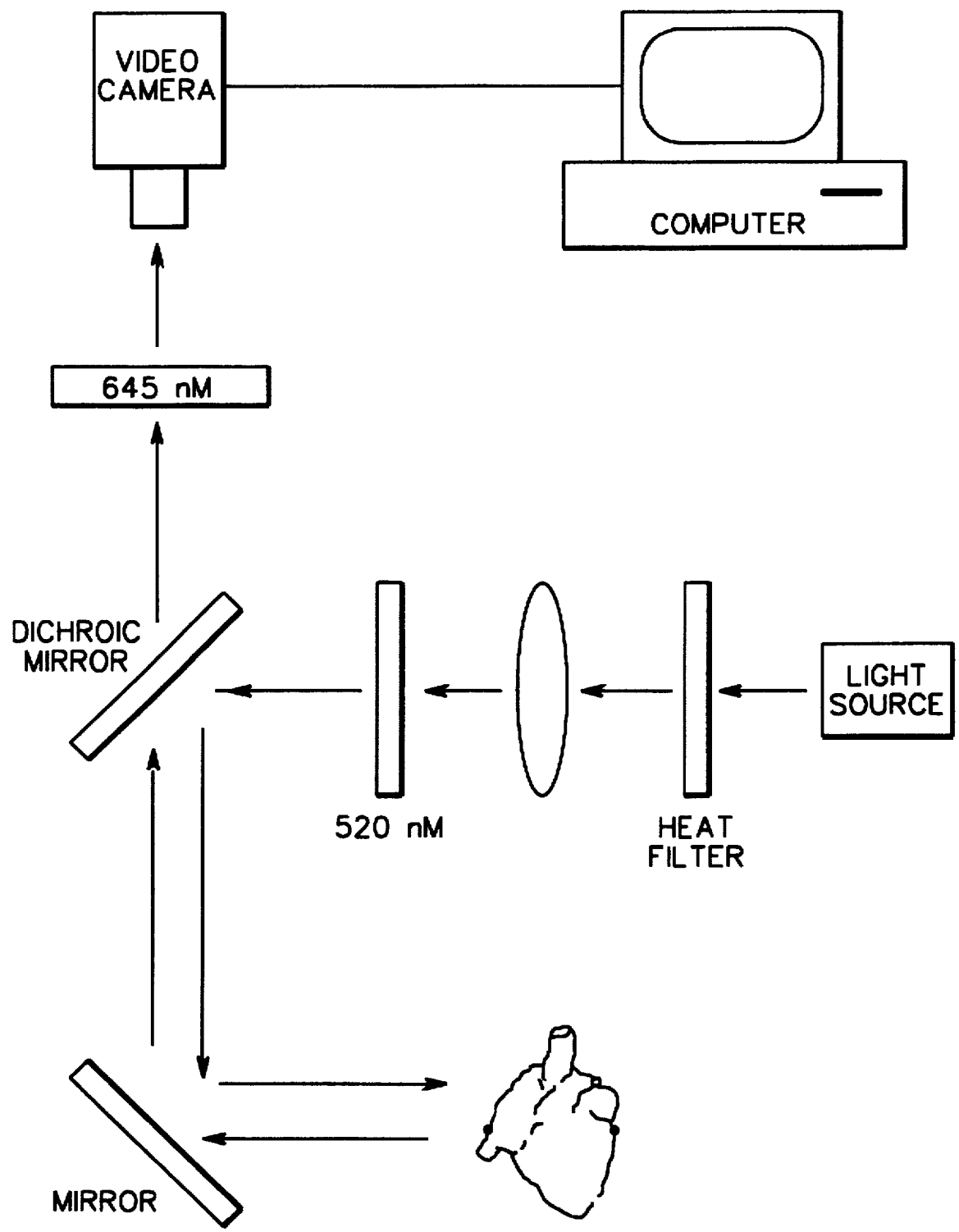
FIG. 5 is a diagram of an experimental setup to test the mechanism of defibrillation in accordance with the present invention.
Figure 6:
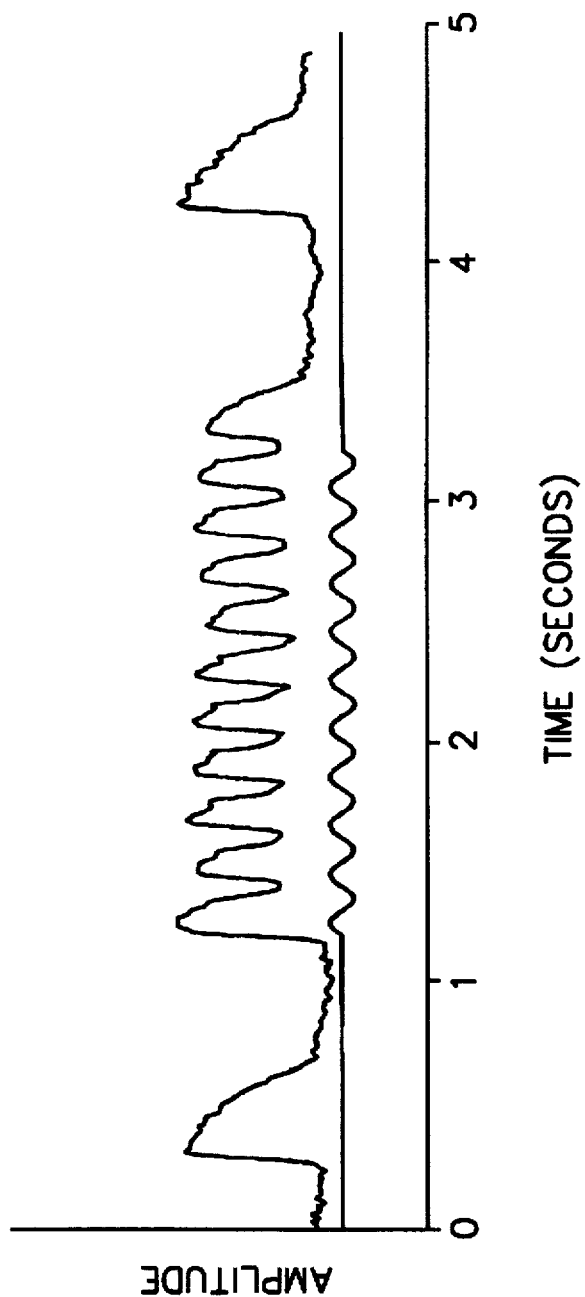
FIG. 6 is a graph of a site on the surface of a rabbit heart entrained to a defibrillation waveform in accordance with the present invention.

To investigate the mechanism of periodic waveforms on the heart, applicants studied the transmembrane potential during long duration (1–2 seconds) sinusoidal (AC) defibrillation shocks. Using high resolution video imaging of the isolated Langendorff-perfused rabbit hearts, applicants studied the transmembrane potential of the entire ventricular epicardial surface during AC field stimulation. The experimental setup, described above, is depicted in FIG. 5. A bolus injection of 15 ml of the dye di-4-ANEPPS (10 μg/ml) dissolved in DMSO was injected into the coronary arteries. Diacetyl monoxime was also added to the solution and perfused throughout the experiment to stop the heart's contraction and prevent mechanical artifacts. The voltage sensitive dye binds to the membranes of cardiac cells, and needs to be excited by light from a powerful source. Light from a tungsten-halogen lamp was collimated and passed through an interference filter (520 nm) together with a heat filter and focused on the surface of a vertically hanging heart. A 50 mm objective lens was used to collect the light emitted by the dye which is linearly related to transmembrane potential. The emitted light was transmitted through an emission filter (645 nm) and projected onto a CCD video camera. The video images (typically 200×100 pixels) of the epicardium were acquired with an A/D frame grabber mounted on a computer which was used to process the imaged data. Frequencies of 1, 2, 5, 10 & 20 Hz were applied during sinus rhythm with amplitudes ranging from 6–62 volts. The fluorescent recordings from each site were converted to membrane potential by assuming resting potential was −80 mV and action potential amplitude was 100 mV during sinus rhythm. The response of the heart was frequency dependent, and after initial depolarization the entire epicardium exhibited oscillations in transmembrane potential as shown in FIG. 6.

All regions were depolarized by the field stimulus and remained above resting potential for the duration of the stimulus. Transmembrane potential shape varied with frequency and along the heart surface. For the highest amplitude stimuli, entrainment of the ventricles was achieved for frequencies of 5, 10 & 20 Hz. Variations in the amplitude and phase of these oscillations were observed spatially at a scale much larger than the cellular scale. Large regions of 1:1 entrainment that were 180° out of phase were observed. Regions in between the areas of 1:1 entrainment exhibited two maxima per cycle. For the 10 Hz field stimulus: 1) at high amplitudes 1:1 entrainment was observed over the entire epicardium; 2) as the strength was lowered to approximately 36 volts, 1:2 entrainment became apparent in some regions; and 3) as the strength was lowered further, the regions with the lowest voltage gradient were no longer entrained to the stimulus. Entrainment during ventricular fibrillation was also achieved including two episodes of successful defibrillation. Currently, electrical defibrillation is accomplished using short duration pulses that terminate all activity. However, our results indicate that periodic field stimulation entrains heart tissue and can result in successful defibrillation utilizing a different mechanism.

Figure 7A:
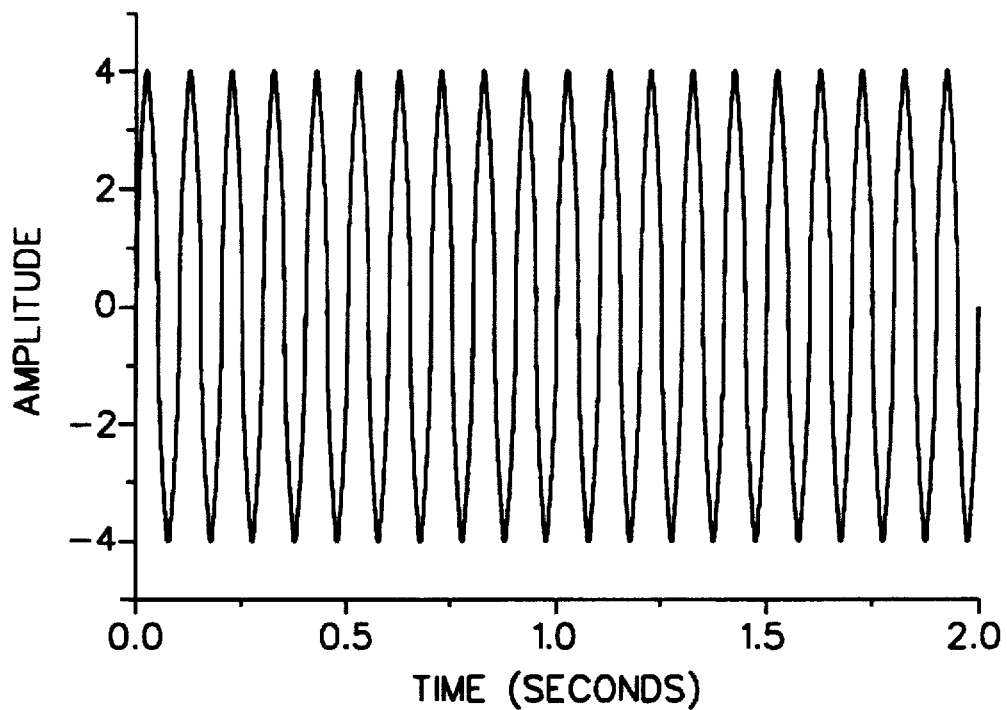
FIG. 7a is a graph of a long duration 10 Hz sinusoidal (AC) waveform for defibrillation in accordance with the present invention.
Figure 7B:
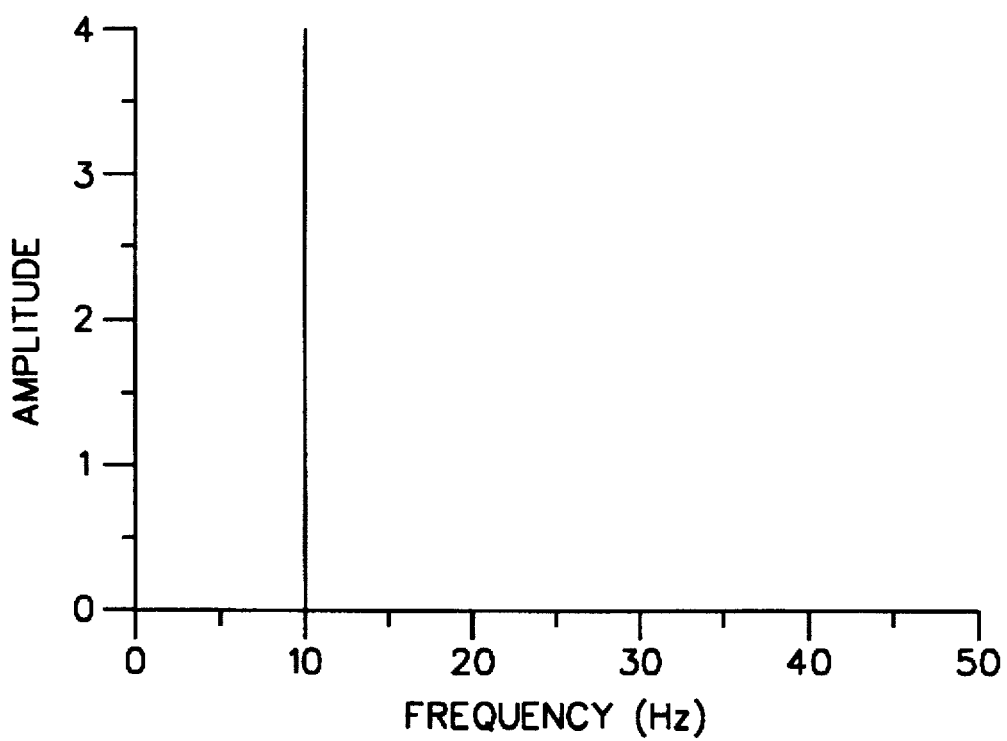
Figure 8A:
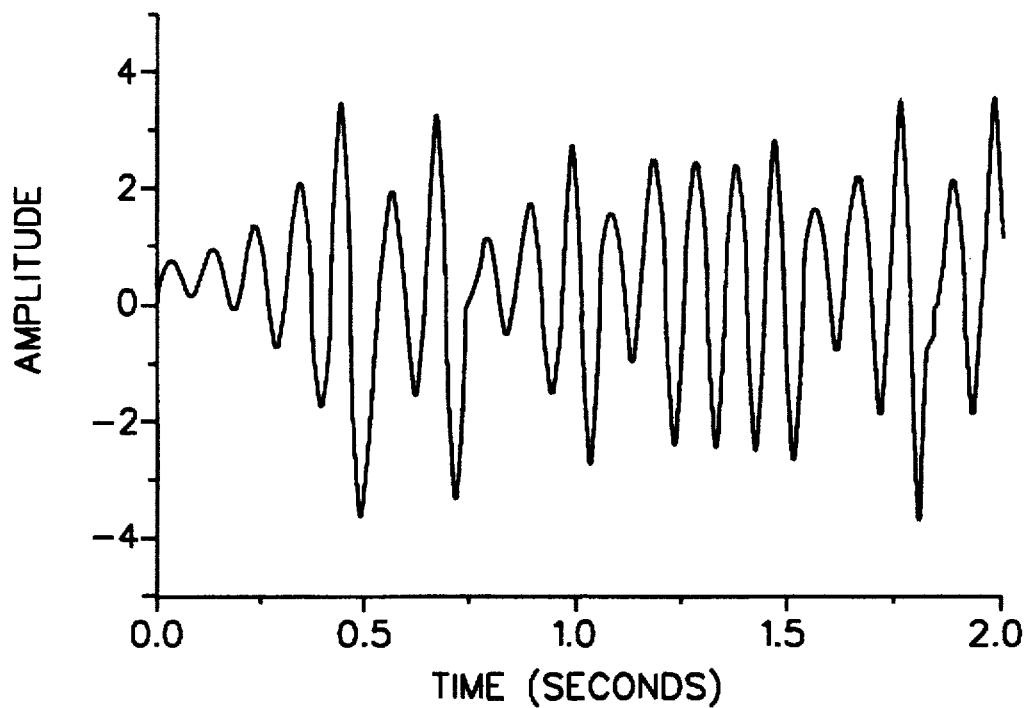
FIG. 8a is a graph of a long duration Rossler-type chaotic waveform with dominant frequency near 10 Hz for defibrillation in accordance with the present invention.
Figure 8B:
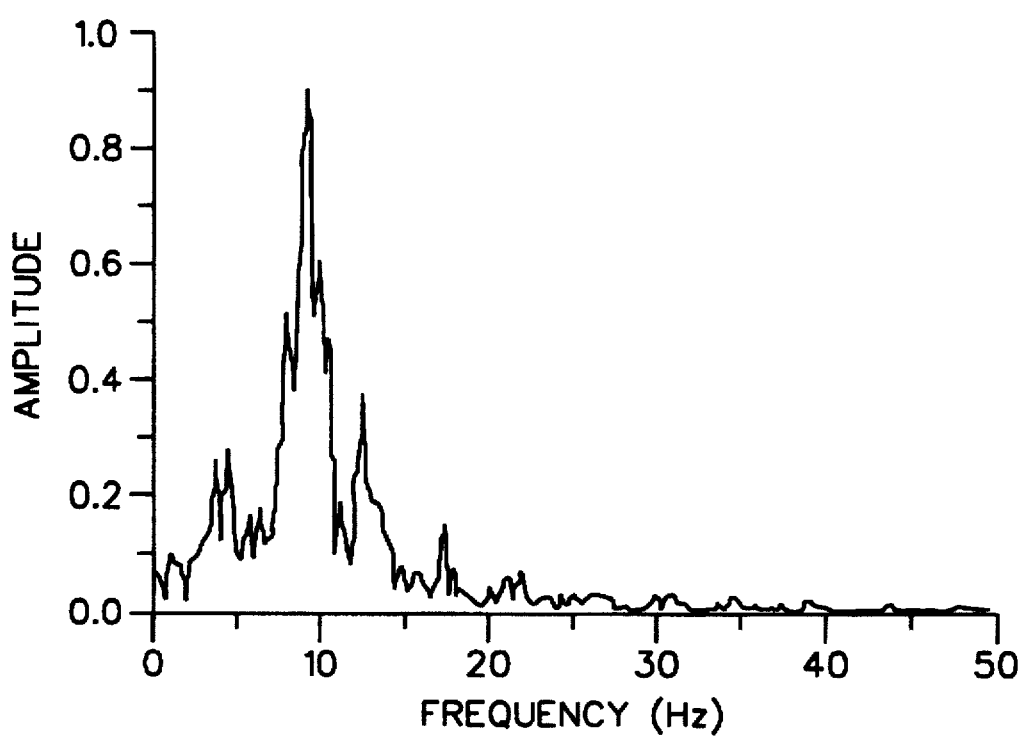

Another long duration 10 Hz sinusoidal waveform in accordance with the present invention is depicted in FIG. 7a and its corresponding frequency spectrum is shown in FIG. 7b. A long duration Rossler-type chaotic waveform (again in accordance with the present invention) is depicted in FIG. 8a, with its frequency spectrum being shown in FIG. 8b. Note the similarities between the frequency spectrum of FIG. 8b and the frequency spectrum of a fibrillating heart depicted in FIG. 1b. By roughly matching the frequencies of these signals, entrainment of the fibrillating heart is achieved at lower power levels than with waveforms previously applied for defibrillation.

Figure 9:
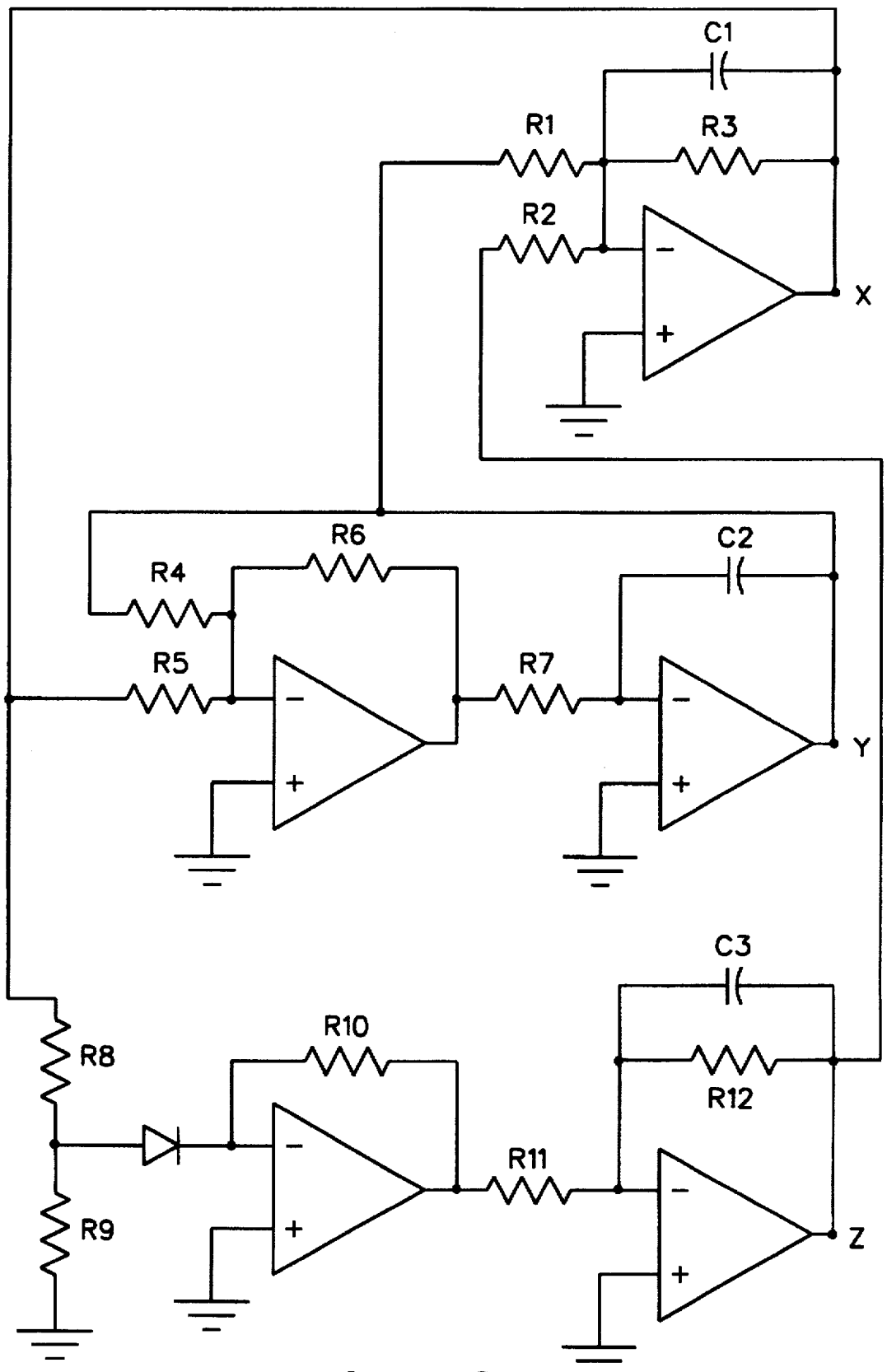

FIG. 9 depicts one circuit embodiment for generating a Rossler-type chaotic waveform as depicted in FIG. 8a. The desired low frequency waveform can be achieved with R1=100 kΩ, R2=100 kΩ, R3=2 MΩ, R4=32 kΩ, R5=10 kΩ, R6=10 kΩ, R7=100 kΩ, R8=10 kΩ, R9=68 kΩ, R10=150 kΩ, R11=100 kΩ, R12=100 kΩ, C1=0.1 µF, C2=0.1 µF and C3=0.1 µF. Resistor R3 can be varied to change the shape of the waveform, for example, R3=450 kΩ provides a sinusoidal output. Capacitors C1, C2 and C3 can be varied to tune the dominant frequency of the chaotic waveform. With C1=C2=C3=0.1 µF, the dominant frequency of the chaotic signal is approximately 10 Hz.

Computer simulations have also been conducted. In one set of experiments, we utilized a monodomain computer model of the heart with realistic geometry made up of 210,000 nodes, each represented by Fitzhugh-Nagumo kinetics. As a first approximation to defibrillation, spatially uniform current was injected across the cell membrane of each node to study the efficacy and mechanisms of AC and DC fibrillation. A spiral wave breakup model was used and scaled such that the dominant frequency of fibrillation was 10 Hz and assuming the total energy for DC fibrillation threshold (DFT) was 15J and the heart resistance was 60Ω. Shocks of AC and DC waveforms were applied such that the initial conditions of the heart were exactly the same. DFT's at four phases of the cardiac cycle were averaged for each waveform. A 6 Hz AC waveform (1.5 cycles) was compared to the DC biphasic rectangular pulse, of total duration 10 milliseconds. Three parameters were compared as shown in Table I below ($p<10^{-5}$ for all three parameters). DC shocks depolarized the cells that were refractory and brought excited cells to resting levels. In comparison, AC shocks accelerated repolarization during the first cycle and then depolarized the heart during the last ½ cycle. The results suggest that low frequency AC defibrillation near the dominant frequency of fibrillation will lower the defibrillation threshold.

TABLE I

|    | peak voltage (V) | total energy (J) | average power (kW) |
|----|------------------|------------------|--------------------|
| DC | 300 ± 6.4        | 15 ± 0.7         | 1.5 ± 0.70         |
| AC | 49.3 ± 4.5       | 5.1 ± 0.9        | 0.02 ± 0.003       |

To summarize, applicants have experimentally and theoretically shown that a low frequency sinusoidal or chaotic Rossler-type waveform can be used to defibrillate cardiac tissue. The precise shape and duration of the waveform do not appear to be critical for lowering the defibrillation threshold. The significant aspect is that the waveform have a dominant frequency near the dominant frequency of the fibrillation episode. The most effective waveforms exhibited a dominant frequency near 10 Hz, but with a range of 2–20 Hz. By decreasing the fibrillation threshold, applicants allow smaller battery packs to be used in internal cardiac defibrillators, and also produce less pain for a patient and cause less damage to heart tissue.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

We claim:

1. A method for defibrillating a heart in fibrillation, comprising the steps of:

detecting fibrillation of the heart; and responsive to said detecting, applying to the fibrillating heart a periodic waveform which entrains the heart thereby producing defibrillation, said periodic waveform having a frequency spectrum with a dominant frequency, said dominant frequency being in the range of 2 Hz–20 Hz.

2. The method of claim 1, wherein said frequency spectrum of said waveform has a range of frequency components, and said dominant frequency comprises one frequency component of said range of frequency components.

3. The method of claim 1, further comprising predetermining a frequency spectrum of a fibrillating human heart and determining therefrom a dominant frequency of fibrillation, said dominant frequency of said waveform applied to said fibrillating heart being near said predetermined dominant frequency of fibrillation of said fibrillating human heart.

4. The method of claim 3, wherein said dominant frequency of said fibrillating human heart is near 10 Hz.

5. A method for defibrillating a heart in fibrillation, comprising the steps of:

detecting fibrillation of the heart; and responsive to said detecting, applying to the fibrillating heart a chaotic waveform having a frequency spectrum with a dominant frequency, said dominant frequency being in a range of 2 Hz–20 Hz.

6. The method of claim 5, wherein said applying comprises applying to the fibrillating heart a Rossler-type chaotic waveform having said dominant frequency.

7. A method for defibrillating a heart in fibrillation, comprising the steps of:

detecting fibrillation of the heart; and responsive to said detecting, applying to the fibrillating heart a sinusoidal-shaped waveform having a frequency spectrum with a dominant frequency, said dominant frequency being in the range of 2 Hz–20 Hz.

8. The method of claim 7, wherein said sinusoidal-shaped waveform of said applying comprises a sinusoidal-shaped waveform of increasing amplitude.

9. A method for defibrillating a heart in fibrillation, comprising the steps of:

detecting fibrillation of the heart; and responsive to said detecting, applying to the fibrillating heart a waveform having a frequency spectrum with a dominant frequency, said dominant frequency being in the range of 2 Hz–20 Hz, and wherein said dominant frequency of said waveform comprises a dominant frequency near a frequency of fibrillation of said fibrillating heart.

10. The method of claim 9, wherein said applying comprises applying to the fibrillating heart said waveform having said dominant frequency for a predefined time interval, wherein said predefined time interval is greater than 0.1 seconds.

11. A method for defibrillating a heart in fibrillation, comprising the steps of:

detecting fibrillation of the heart; and responsive to said detecting, applying to the fibrillating heart a waveform having a frequency spectrum with a dominant frequency and a subordinate frequency, said dominant frequency being lower than said subordinate frequency within said waveform.

12. A defibrillator for defibrillating a fibrillating heart, said defibrillator comprising:

electrical generating means for producing a periodic waveform having a frequency spectrum with a dominant frequency, said dominant frequency being in the range of 2 Hz–20 Hz; and means for delivering said waveform to electrically entrain the fibrillating heart, thereby causing defibrillation of the heart.

13. The defibrillator of claim 12, wherein said electrical generating means further comprises means for producing said waveform having said dominant frequency and a duration longer than 0.1 seconds.

14. The defibrillator of claim 12, wherein said electrical generating means comprises producing said waveform to have multiple frequency components, said dominant frequency comprising one frequency component of said multiple frequency components.

15. The defibrillator of claim 12, wherein said dominant frequency of said waveform produced by said electrical generating means comprises a frequency near 10 Hz.

16. A defibrillator for defibrillating a fibrillating heart, said defibrillator comprising:

electrical generating means for generating a Rossler-type chaotic waveform having a dominant frequency, said dominant frequency being near a frequency of fibrillation of the fibrillating heart and in the range of 2 Hz–20 Hz; and means for delivering said waveform to provide electrical shock to the fibrillating heart, thereby causing defibrillation of the heart.

17. A defibrillator for defibrillating a fibrillating heart, said defibrillator comprising:

electrical generating means for generating a sinusoidal-shaped waveform having a frequency spectrum with a dominant frequency, said dominant frequency being in the range of 2 Hz–20 Hz; and means for delivering said waveform to electrically entrain the fibrillating heart, thereby causing defibrillation of the heart.

* * * * *